(12) United States Patent
Wijshoff et al.

(10) Patent No.: US 11,793,466 B2
(45) Date of Patent: Oct. 24, 2023

(54) SENSOR DEVICE AND METHOD, DEVICE AND METHOD FOR COMMUNICATION WITH THE SENSOR DEVICE

(71) Applicant: KONINKLIJKE PHILIPS N.V., Eindhoven (NL)

(72) Inventors: Ralph Wijshoff, Munstergeleen (NL); Theodorus Jansen, Deurne (NL); Anthonius Janssen, Berghem (NL); Joseph Fallon, Boxford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 16/323,806

(22) PCT Filed: Aug. 7, 2017

(86) PCT No.: PCT/EP2017/069887
§ 371 (c)(1),
(2) Date: Feb. 7, 2019

(87) PCT Pub. No.: WO2018/029127
PCT Pub. Date: Feb. 15, 2018

(65) Prior Publication Data
US 2019/0175116 A1    Jun. 13, 2019

Related U.S. Application Data

(60) Provisional application No. 62/374,031, filed on Aug. 12, 2016.

(30) Foreign Application Priority Data

Aug. 30, 2016 (EP) ..................................... 16186224

(51) Int. Cl.
A61B 5/00 (2006.01)
A61B 5/1455 (2006.01)
A61B 5/024 (2006.01)

(52) U.S. Cl.
CPC .......... *A61B 5/7203* (2013.01); *A61B 5/0059* (2013.01); *A61B 5/02416* (2013.01);
(Continued)

(58) Field of Classification Search
CPC . A61B 5/7203; A61B 5/0059; A61B 5/02416; A61B 5/7214; A61B 5/7228;
(Continued)

(56) References Cited

U.S. PATENT DOCUMENTS 5,588,427 A    12/1996 Tien
8,447,372 B2    5/2013 Veen
(Continued)

FOREIGN PATENT DOCUMENTS

JP    2005124903 A    5/2005
WO    2009/153700    12/2009
(Continued)

OTHER PUBLICATIONS

John Allen: "Photoplethysmography and its application in clinical physiological measurement"; Physiol. Meas. 28 (2007) R1-R39.

*Primary Examiner* — Patrick Fernandes
*Assistant Examiner* — Joseph A Tombers (57) ABSTRACT

The present invention relates to a sensor device (100, 101, 102, 103) for sensing physiological information of a subject. To efficiently avoid or reduce ambient interference, the sensor device comprises a communication unit (7) for receiving, from an external source, context information indicating one or more of a modulation mode, settings of an interference reduction algorithm, and spectral information indicating an ambient light spectrum, said spectral informa-
(Continued)

tion allowing the sensor device to determine the modulation mode and/or settings of an interference reduction algorithm, one or more light emitters (1, 2) for emitting modulated light onto the tissue of the subject, and a light detector (4) for detecting light which is transmitted through the tissue or/and which is reflected from the tissue. The sensor device further comprises a light modulator (6) for modulating light in accordance with the modulation mode indicated by or determined from the received context information and a light demodulator (11) for demodulating the detected light in accordance with the modulation mode used by the light modulator for modulating light and/or a processing unit (5) for performing an interference reduction algorithm for reducing ambient light interference with settings indicated by or determined from the received context information.

14 Claims, 3 Drawing Sheets

(52) U.S. Cl.
CPC ........ *A61B 5/14551* (2013.01); *A61B 5/7214* (2013.01); *A61B 5/7228* (2013.01); *A61B 5/6826* (2013.01); *A61B 2560/0247* (2013.01); *A61B 2560/0276* (2013.01)

(58) Field of Classification Search
CPC ........ A61B 5/14551; A61B 2560/0276; A61B 5/6826; A61B 2560/0247
See application file for complete search history.

(56) References Cited

U.S. PATENT DOCUMENTS

| | | |
|---|---|---|
| 8,471,713 B2 | 6/2013 | Poeze |
| 2007/0230941 A1 | 10/2007 | Smith |
| 2008/0076986 A1 | 3/2008 | Pav |
| 2008/0167541 A1 | 7/2008 | Takala |
| 2009/0069642 A1* | 3/2009 | Gao ................ H04L 67/125 600/300 |
| 2010/0087718 A1 | 4/2010 | Gonopolskiy |
| 2010/0094106 A1* | 4/2010 | Kiani ............... A61B 5/6826 600/310 |
| 2011/0092824 A1* | 4/2011 | Veen ............... A61B 5/14551 600/477 |
| 2011/0109459 A1* | 5/2011 | Poeze .............. G01R 13/0281 324/613 |
| 2012/0136257 A1* | 5/2012 | Krishnan ......... A61B 5/02416 600/476 |
| 2014/0275850 A1 | 9/2014 | Venkatraman |
| 2014/0278238 A1 | 9/2014 | Teague |
| 2015/0012231 A1 | 1/2015 | Poeze |
| 2015/0018649 A1* | 1/2015 | Lisogurski ........... H05B 45/36 600/323 |
| 2015/0148636 A1* | 5/2015 | Benaron .......... A61B 5/02405 600/328 |
| 2016/0018257 A1 | 1/2016 | Mirov |
| 2017/0065230 A1* | 3/2017 | Sinha ................. G16H 50/20 |

FOREIGN PATENT DOCUMENTS

| | | |
|---|---|---|
| WO | 2011/011730 | 1/2011 |
| WO | 2011/117780 | 9/2011 |

* cited by examiner

SENSOR DEVICE AND METHOD, DEVICE AND METHOD FOR COMMUNICATION WITH THE SENSOR DEVICE

CROSS REFERENCE TO RELATED APPLICATIONS

This application is the U.S. National Phase application under 35 U.S.C. § 371 of International Application No. PCT/EP2017/069887 filed Aug. 7, 2017, published as WO 2018/029127 on Feb. 15, 2018, which claims the benefit of European Patent Application Number 16186224.8 filed Aug. 30, 2016 and U.S. Provisional Patent Application No. 62/374,031 filed Aug. 12, 2016. These applications are hereby incorporated by reference herein.

FIELD OF THE INVENTION

The present invention relates to a sensor device for sensing physiological information of a subject. Further, the present invention relates to a device for communication with a sensor device for monitoring physiological information of a subject. Still further, the present invention relates to corresponding methods.

BACKGROUND OF THE INVENTION

Pulse oximetry is widely applied to measure pulse rate (PR), oxygen saturation (SpO2) or other physiological information (also called vital signs). Pulse oximeters (or, more generally, sensor devices) are used in hospitals, but also in ambulatory settings, e.g., at home. Pulse oximeters make use of the optical technology called photoplethysmography (PPG). PPG measures cardiac-induced changes in arterial blood volume by emitting light through tissue. A pulse oximeter uses multiple light sources to obtain PPG signals at least at two different wavelengths. These light sources are multiplexed/modulated to measure the PPG signals with a single photodiode.

Conventionally, the light modulation schemes of pulse oximeters are static and have been designed to prevent interference from 50 Hz and 60 Hz mains components and their harmonics. Nowadays, not mains frequency based electronic light dimming and new light sources, such as LED lighting, and modulated lighting systems, which encode information in the light, cause interference at other frequencies than the frequencies related to mains. Moreover, the frequency of the interference can change over time, e.g., when it depends on specific settings of a lamp such as the amount of dim. Therefore, the conventional schemes cannot suppress interference from new lighting solutions.

WO 2011/117780 A1 discloses measuring the interfering light frequencies by adding a dark channel, i.e., measuring the photodiode current with the LEDs switched off. Via adaptive filtering the ambient light interference in each of the PPG signals can then be suppressed to some extent. However, such an adaptive filter will not completely remove the interference. WO 2009/153700 A1 discloses measuring the ambient light interference via spectral analysis and adjusting the Time Domain Multiplexing (TDM) or Frequency Domain Multiplexing (FDM) modulation schemes accordingly to avoid using the spectral ranges which are polluted by ambient light interference.

Further, WO 2011/011730 A1 discloses a system for detecting and calculating the level of ambient and/or environmental noise, such as electromagnetic interference generated by electric power lines, ambient lights, light dimmers, television or computer displays, power supplies or transformers, and medical equipment. The system comprises a monitor and a sensor. In some embodiments, the system performs frequency analysis on the interference signal detected by light photodetectors and determines the power of the interference signal concentrated in the analyzed frequency bands. The worst-case interference level can be determined by selecting the maximum from the computed power values. In some embodiments, the determined interference signal power can be compared with the noise tolerance of a patient monitoring system configured to reliably and non-invasively detect physiological parameters of a user. In the disclosed system the modulation, demodulation and processing is performed in the monitor.

The known approaches, however, have disadvantages. Adaptation to lighting conditions requires periodic measurement and analysis of the environmental light, which consumes power. Further, in some conditions it may not be possible to perform reliable photoplethysmographic/pulse oximetry measurements given the interference from the light conditions at hand.

SUMMARY OF THE INVENTION

It is an object of the present invention to provide a sensor device and method as well as a device and method for communication with such a sensor device, which efficiently avoid or reduce interference from other sources, such as lighting solutions.

In a first aspect of the present invention a sensor device for sensing physiological information of a subject is presented comprising
 a communication unit for receiving, from an external source, context information indicating one or more of
  a modulation mode,
  settings of an interference reduction algorithm, and
  spectral information indicating an ambient light spectrum, said spectral information allowing the sensor device to determine the modulation mode and/or settings of an interference reduction algorithm,
 one or more light emitters for emitting modulated light onto the tissue of the subject, and
 a light detector for detecting light which is transmitted through the tissue or/and which is reflected from the tissue, further comprising
 a light modulator for modulating light in accordance with the modulation mode indicated by or determined from the received context information and a light demodulator for demodulating the detected light in accordance with the modulation mode used by the light modulator for modulating light and/or
 a processing unit for performing an interference reduction algorithm for reducing ambient light interference with settings indicated by or determined from the received context information.

In a further aspect of the present invention a device for communication (also called "communication device" hereinafter) with a sensor device for monitoring physiological information of a subject is presented comprising
 a context information obtaining unit for obtaining context information indicating one or more of
  a modulation mode,
  settings of an interference reduction algorithm, and
  spectral information indicating an ambient light spectrum, said spectral information allowing the sensor device to determine the modulation mode and/or settings of an interference reduction algorithm, a communication unit for transmitting to the sensor device the obtained context information.

In yet further aspects of the present invention, there are provided corresponding methods.

Preferred embodiments of the invention are defined in the dependent claims. It shall be understood that the claimed methods have similar and/or identical preferred embodiments as the claimed devices, in particular as defined in the dependent claims and as disclosed herein.

The present invention is based on the idea to receive, instead of to measure the interference spectrum itself, information about interference and the optimum modulation mode (sometimes also called modulation scheme) to use from an external source, e.g. the proposed device for communication with the sensor device, to which it is connected via a (wired or wireless) communication channel. The information may hereby be received in advance so that the sensor device can be preconfigured in a particular setting, or the information may be received as a current measurement to directly set the sensor device in a favorable modulation mode.

The received context information may include modulation information indicating a modulation mode, i.e. the external source determined the best modulation mode, e.g., from measured spectral information. Additionally or instead, the received context information may include spectral information indicating an ambient light spectrum, said spectral information allowing the sensor device to determine the modulation mode. Further, the received context information may include settings of an interference reduction algorithm and/or sensor type information. For instance, an adaptive filtering scheme may be applied, as example of an interference reduction algorithm, to remove the interference. The sensor type provides information about the achievable performance, which could be recorded in a table with achievable thresholds for specific sensor types.

Receiving and using such context information, e.g. about what modulation mode or what interference reduction algorithm to use, can be more power efficient compared to known methods. Preconfiguring a sensor device with the interference spectra present is most power efficient. By reporting the information about possible interferences, e.g. the modulation information and/or spectral information, to the user as proposed in an embodiment, the lighting conditions may be changed to enable reliable measurements.

Thus, according to the present invention knowledge about ambient light interference is used, which knowledge can be obtained in various ways, as is the subject of different embodiments. Said different ways include, but are not limited to measurement and spectral analysis of the ambient light, built-in/stored interference spectra, a photoplethysmography system with an adjustable modulation scheme (the photoplethysmography system can receive ambient light interference information from multiple systems, e.g., a pulse oximeter or a sports watch with an optical heart rate measurement), a communication channel through which the various devices/systems can communicate with each other.

In an embodiment the sensor device may further comprise a processing unit for determining a vital parameter of a subject from the demodulated light. While in some embodiments the vital parameter (e.g., pulse rate, SpO2, etc.) may be determined outside of the sensor device, e.g., in a connected patient monitor or measurement module, in this embodiment the sensor device itself can determine the desired vital parameter. The determined vital parameter can then be shown on a small display, or transmitted to a patient monitor or a measurement module or a (caregiver's) user device for display, or to any other external entity for further use.

In another embodiment the sensor device may further comprise a processing unit for determining from the received spectral information the modulation mode and/or settings of an interference reduction algorithm, for which ambient light interference is minimized or is below a predetermined threshold or a threshold determined from the context information such as the sensor type. Hence, the sensor device itself determines the optimum modulation mode or interference reduction algorithm. The threshold is preferably determined in advance, e.g. by simulations or measurements. The threshold may e.g. be set in absolute units or related to the level of the physiological signal of interest. Furthermore, with this embodiment the sensor type which is applied to the patient can be determined or this information can be obtained as part of the context information. Further, with this embodiment the threshold can be adjusted dependent on the known ambient shielding performance or "ambient light sensitivity" of the applied sensor.

The light detector, which may e.g. be a photodiode, may be configured to measure the ambient light spectrum while no light is emitted by said light emitter, which may e.g. be an LED, and the sensor device may further comprise a processing unit for determining from the measured ambient light spectrum the modulation mode and/or settings of an interference reduction algorithm, for which ambient light interference is minimized or is below a predetermined threshold or a threshold determined from the context information such as the sensor type. This enables the sensor device to verify or adjust any received context information like modulation and spectrum information based on actual and up-to-date measurements made by the sensor device itself, which exactly reflect the potential interference at the location of the sensor device.

In another embodiment said light detector is configured to measure the ambient light spectrum while no light is emitted by said light emitter, and said communication unit is configured to transmit further spectral information indicating the measured ambient light spectrum to an external entity, e.g. a patient monitor. The determination of the optimum modulation mode and/or settings of an interference reduction algorithm may thus be done by the external entity and may then be communicated to the sensor device, which thus does not require using power to analyze the spectral information. A processing unit may still be required to determine the spectrum, or efficiently communicate the measured data, or determine a physiological parameter.

The sensor device may further comprise a processing unit for determining if sufficient bandwidth is available for emitting light by the light emitter with ambient light interference below a predetermined threshold, possibly after application of an interference reduction algorithm. Hereby, the sensor device may further comprise an alarm unit for issuing an alarm if it is determined that insufficient bandwidth is available for emitting light by the light emitter with ambient light interference below a predetermined threshold, possibly after application of an interference reduction algorithm. An exemplary sufficient bandwidth may be e.g. 10-30 Hz centered around a carrier frequency depending on the type of application. Hence, if ambient light interference cannot be sufficiently prevented by adjusting the modulation mode or cannot be sufficiently reduced by the filtering scheme, an interference alarm is issued to inform the user or caregiver that no reliable measurement is possible given the lighting conditions at hand.

In another embodiment said processor may be configured to determine if ambient light interference is below a threshold and to set said threshold in accordance with the sensor type information. The sensor type information may include information whether it is a transmissive or reflective sensor, the amount of shielding for ambient light, information about the site (e.g. finger, forehead, earlobe, nasal septum, alar wing, foot, etc.), information about the patient category (e.g. neonate, child, adult) and/or information about the manufacturer and the model.

The various processing units of the sensor device may be implemented by the same or different elements and may use hardware, software or a combination of soft- and hardware, e.g. a programmed processor.

The device for communication (also called communication device herein) with the above described sensor device comprises a context information obtaining unit for obtaining (i.e. acquiring, receiving or retrieving) context information indicating one or more of a modulation mode, settings of an interference reduction algorithm, sensor type information, and spectral information indicating an ambient light spectrum, said spectral information allowing the sensor device or the communication device to determine the modulation mode and/or settings of an interference reduction algorithm. Further, the communication device comprises a communication unit for transmitting to the sensor device the obtained context information. The communication device and the sensor device may e.g. be connected wirelessly or in a wired manner, e.g. via a communications network, a computer network, WLAN, Bluetooth, etc., and the communication unit may be adapted accordingly for transmitting the desired information to the sensor device.

In a preferred embodiment the context information obtaining unit comprises a light detector, e.g. a photodiode, for detecting an ambient light spectrum and the communication device further comprises an analysis unit for analyzing the detected ambient light spectrum and generating said context information. This provides an efficient but simple solution for obtaining the context information.

The communication device may further comprise a processing unit for determining from the obtained context information the modulation mode and/or the settings of an interference reduction algorithm, for which ambient light interference is minimized or is below a predetermined threshold.

Said processing unit may further be configured to take previously obtained spectral information and/or a previously determined modulation mode and/or previously determined settings of an interference reduction algorithm into account in determining the modulation mode and/or the settings of an interference reduction algorithm. This further improves the determination of the modulation mode and/or the settings of an interference reduction algorithm, i.e. the processing unit may be configured as a learning system.

The communication device may further comprise a processing unit for determining if sufficient bandwidth is available for emitting light by the light emitter of the sensor device with ambient light interference below a predetermined threshold, possibly after application of an interference reduction algorithm, and an alarm unit for issuing an alarm if it is determined that insufficient bandwidth is available for emitting light by the light emitter of the sensor device with ambient light interference below a predetermined threshold, possibly after application of an interference reduction algorithm. For instance, a caregiver or other staff may be informed to take measures to change the ambient lighting conditions to make sure that measurements can be taken with less ambient light interference, or to replace the sensor by a sensor which has better shielding against ambient lighting. This prevents unreliable measurements made while an excessive ambient light level is present.

In an embodiment the communication device is a lighting apparatus, wherein said context information obtaining unit comprises an interface for receiving or measuring the emission spectrum of the lighting apparatus and generating said context information (in particular spectral information) from said emission spectrum. The lighting apparatus generally knows its own emission spectrum and can thus forward this information so that the spectral information or other context information (e.g., modulation information) can be determined in an easy but accurate manner.

In another embodiment said context information obtaining unit is configured to receive spectral information indicating an ambient light spectrum from said sensor device or from a light detector.

The various processing units of the communication device may be implemented by the same or different elements and may use hardware, software or a combination of soft- and hardware, e.g. a programmed processor.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
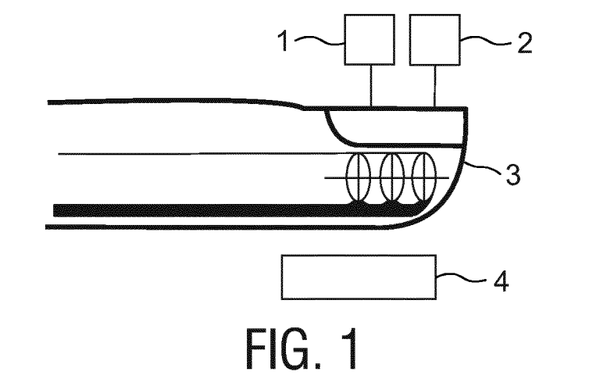
FIG. 1 shows a typical setup for transmission pulse oximetry.

FIG. 1 shows a typical setup for transmission pulse oximetry: A red light source 1 and a near-infrared (IR) light source 2 are used for irradiating red light of, e.g. 660 nm, and near-IR light of, e.g. 940 nm, onto tissue of a patient, i.e. onto a finger 3. The part of the light which is transmitted through the finger 3 is then collected with a common light detector 4, e.g. a photodiode. More than two wavelengths, e.g. four, eight or twelve wavelengths, may be used as well in pulse oximetry.

Figure 2:
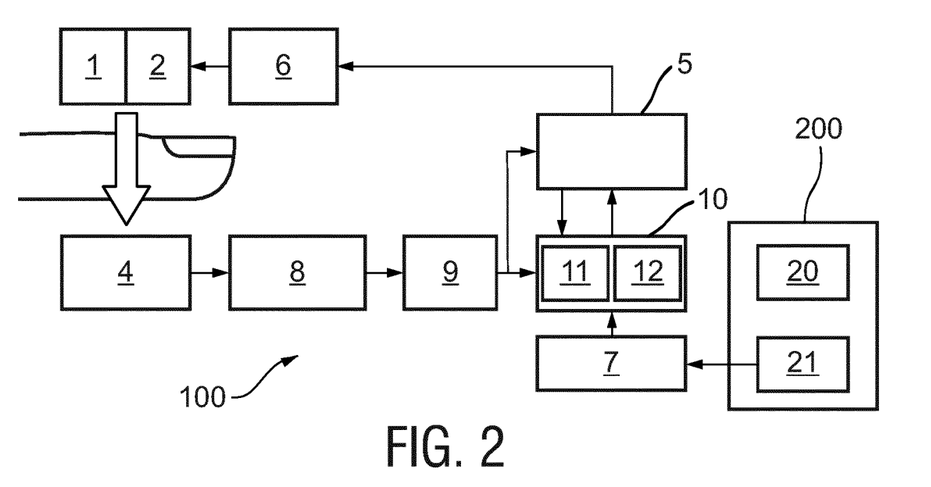
FIG. 2 shows a schematic diagram of a first embodiment of a sensor device, in particular for transmission pulse oximetry, and a communication device according to the present invention.

FIG. 2 depicts a general block diagram of a transmission pulse oximeter, as an example of a sensor device 100, according to a first embodiment of the present invention. The sensor device 100 comprises a processing unit 5 that adjusts the parameters of a light modulator 6 which acts a pulse controller and modulates the light sources 1, 2. The configuration of the light modulator 6 depends on the specific multiplexing scheme applied, e.g. in case of TDM the light sources 1, 2 are activated alternatingly whereas for FDM the light sources 1, 2 radiate light with different modulation frequencies. In case of FDM, the light sources can also simultaneously radiate light with different modulation frequencies, but this requires the light sources not to be configured anti-parallel. The reason for the multiplexing scheme is that in this way the same light detector 4 can be used to estimate the attenuation of the light from both light sources 1, 2.

The light detector 4 detects the light that has propagated through the medium of the finger 3 and converts it into an electrical signal. This signal is then pre-processed by a signal-conditioning block 8, which comprises analog amplifiers and filters, which make the signal suitable for conversion to the digital domain by an analog-to-digital converter (ADC) 9. Correlators 10, each comprising a demodulator 11 and a demultiplexer 12, are used to simultaneously demodulate and demultiplex the detected light, and the results are presented to the processing unit 5, which determines the parameters of interest by evaluating the transmitted and demodulated signals.

For that, the sensor device 100 comprises a communication unit 7 for receiving context information indicating the modulation mode, settings of an interference reduction algorithm, sensor type information, and/or spectral information indicating an ambient light spectrum, said spectral information allowing the sensor device 100 to determine the modulation mode or to determine the filtering scheme to reduce the interference. This information is received from a communication device 200, which may e.g. be a patient monitor or a lighting apparatus. The communication device 200 particularly comprises a context information obtaining unit 20 for obtaining context information, e.g. spectral information indicating an ambient light spectrum, and a communication unit 21 for transmitting to the sensor device the context information. The sensor device 100 can e.g. use a modulation mode being provided to the sensor device 100 for modulating light in accordance with the modulation mode. Alternatively, the sensor device 100 can use the context information to determine the optimum filtering scheme to reduce the interference.

Figure 3:
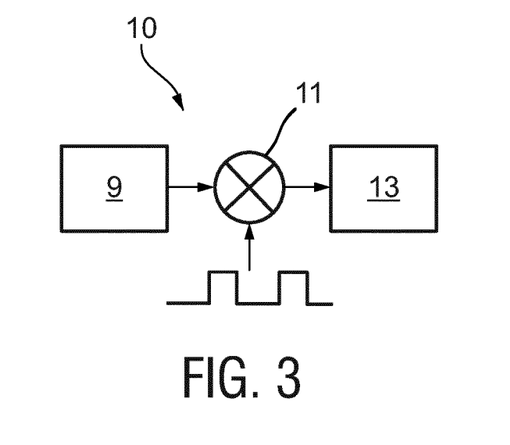
FIG. 3 shows a demodulator with a periodic square wave reference signal.

The modulation mode used according to the various embodiments of the present invention is independent of the specific multiplexing technique applied, since all attenuation measurement methods incorporate a certain modulation method. To simplify matters, the description of the following embodiments is restricted to a single light source, as may also be used in an embodiment of the proposed sensor device, thereby disregarding the specific demultiplexing method. For a single light source, only one correlator 10 is necessary. This correlator 10 then simply equals a demodulator 11, such as depicted in FIG. 3. Here, the information on the light attenuation becomes present in the base-band by multiplying the received signal with a local reference of the same fundamental frequency (fm=1/Tm). Subsequently, only the base-band signal is preserved by passing the signal through a low-pass filter 13, thereby disregarding out-of-band interference.

It should be noted that the square wave shown in FIG. 3 is only illustrative, as any periodic signal can be applied to both modulate the light sources 1, 2 and demodulate the received signal as long as the fundamental frequencies and/or harmonics coincide. Further, according to embodiments, the sensor device may be configured, instead of a pulse oximeter, as another type of device with a photoplethysmograph, such as a sports watch, a heart rate measuring device, a wearable device, a smartphone etc. with an optical measurement for sensing physiological information of a subject, such as a patient, a person doing sports, a neonate, etc., or of an animal such as a pet.

In the following, further embodiments of the sensor device and the communication device are shown, which are partly simplified by not explicitly showing all elements, such as the light emitter(s) and light detector(s) as e.g. shown in FIGS. 1 and 2.

Figure 4:
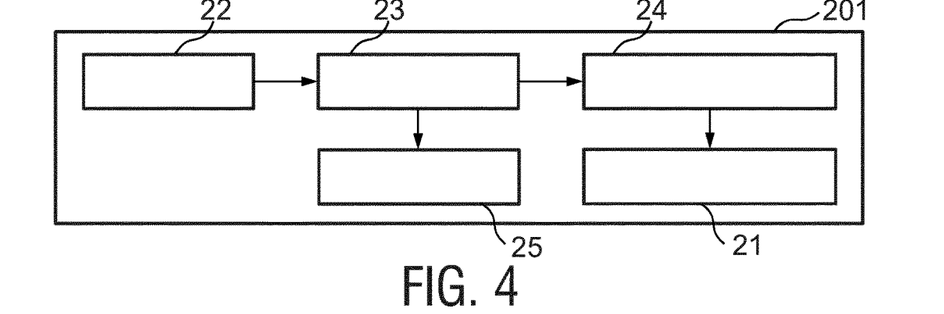
FIG. 4 shows a schematic diagram of a second embodiment of a sensor device and a communication device according to the present invention.

A second embodiment of a communication device 201 is illustrated in FIG. 4, which is implemented as a patient monitor in this embodiment. Here, the analysis of the ambient light spectrum and the subsequent selection and adjustment of the modulation scheme has been incorporated in the patient monitor 201. The patient monitor 201 comprises a photodiode 22 (in general a light detector), e.g. as an implementation of the spectral information obtaining unit 20. An analyzer 23 analyses the ambient light spectrum and finds a suitable part in the spectrum containing the required bandwidth with a minimum amount of ambient light interference, possibly after the application of an interference reduction algorithm. Based on the analysis the processing unit 24 determines the most appropriate modulation mode to use with the optimal parameters, optionally also taking into account previously measured interference spectra (i.e. spectral history). Subsequently, the communication unit 21 transmits (e.g. broadcasts) a message to selected or, preferably, all sensor devices (e.g. pulse oximeters and/or other sensor devices) in the vicinity e.g. in the same room, containing the context information, e.g. including instructions of the optimal modulation mode which should be selected and executed by the sensor devices. Alternatively or additionally, the processing unit 24 can determine the optimum parameters of an interference reduction algorithm, which settings are also transmitted by communication unit 21.

The patient monitor 201 can perform ambient light spectral analysis on short intervals, e.g., every 0.5 s. Measurement of ambient light can be performed using, e.g., a photodiode positioned on top of the patient monitor or next to the display of the patient monitor.

Because a patient monitor 201 can remain in the same room, it can keep a history of ambient light spectra, for instance in the analysis unit 23. In this way, the patient monitor 201 can also store the interference from, e.g., a reading light which is only switched on occasionally. By taking into account the history in the determination of the most suitable modulation mode, the patient monitor can prevent disturbances from light sources which are switched on only occasionally.

If the analysis of the current ambient light spectrum shows that there is not sufficient bandwidth available with the minimum required level of interference, possibly after application of an interference reduction algorithm, the patient monitor 201 can issue a visual and/or audible interference alarm by an optional alarm unit 25.

Using the communication device, e.g. a patient monitor, for analysis of ambient light spectra is particularly suitable when battery-powered sensor devices are used. In this case, the individual sensor devices do not have to use power for the ambient light spectral analysis, and only have to receive instructions from the communication device, which is e.g. powered by mains. It would be a waste of resources if all battery-powered sensor devices in a room individually analyze the ambient light spectrum, all arriving at the same conclusion, as exposure to ambient light is an overall environmental condition holding for all sensor devices in a room.

Figure 5:
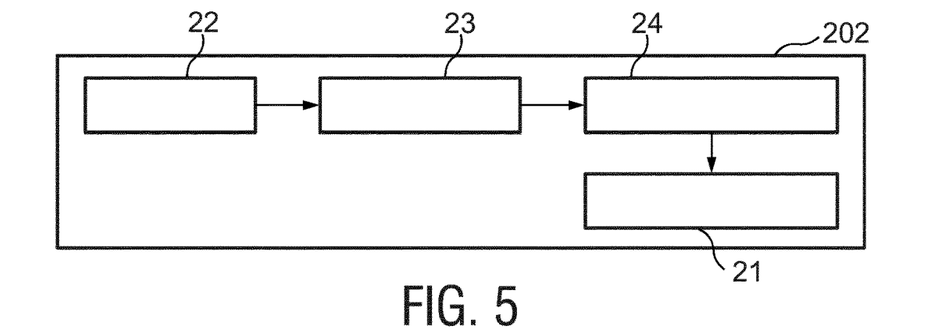
FIG. 5 shows a schematic diagram of a third embodiment of a sensor device and a communication device according to the present invention.

A third embodiment of a communication device 202 is illustrated in FIG. 5, which is implemented as a dedicated small device that is e.g. placed in and powered by a wall socket. This small device 202 comprises a light detector 22 and an analysis unit 23, like the patient monitor 201 to determine the most appropriate modulation mode to use given the ambient light spectrum. The processing unit 24 determines the optimum modulation parameters such as the repetition frequency in a Time Division Multiplexing scheme, the frequencies of operation in a Frequency Division Multiplexing scheme, or the modulation frequency of a Quadrature Amplitude Modulation mode. Alternatively or additionally, the processing unit 24 can determine the optimum parameters of an interference reduction algorithm to reduce the effect of interference below a required level. The modulation mode and optimal parameters are communicated to the sensor devices in the vicinity by the communication unit 21. This solution could be attractive in, e.g., a hallway, where ambulant patients are passing by with a wearable battery-powered sensor solution.

Figure 6:
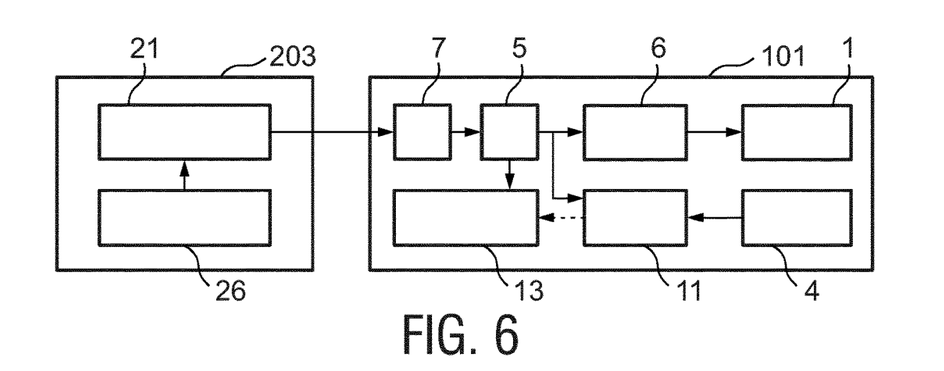
FIG. 6 shows a schematic diagram of a fourth embodiment of a sensor device and a communication device according to the present invention.

A fourth embodiment of a communication device 203 and another embodiment of a sensor device 101 are illustrated in FIG. 6. Here, the communication unit 203 is implemented as lighting apparatus (or part of a lighting system). A smart lighting apparatus or a smart lighting system generally knows the (time-varying) emission spectrum that it uses and communicates this to a sensor device, which can receive the emission spectra of multiple smart lighting apparatus and/or systems. Based on the received interference spectra, the sensor device 101, in particular the processing unit 5, determines the most appropriate modulation mode with the optimal parameters and/or the optimum parameters of an interference reduction algorithm. If the sensor device 101 is unable to determine a modulation and/or interference reduction which reduces the amount of ambient light interference to a required minimum (i.e. below a predetermined threshold), or if the acquired detection signals (as acquired by the light detector) or information (e.g. a vital sign) derived from the detection signals show that the ambient light interference is too large or that the acquired detection signals or the information derived there from is disturbed and/or not reliable, an interference alarm may be issued by an alarm unit 13.

Figure 7:
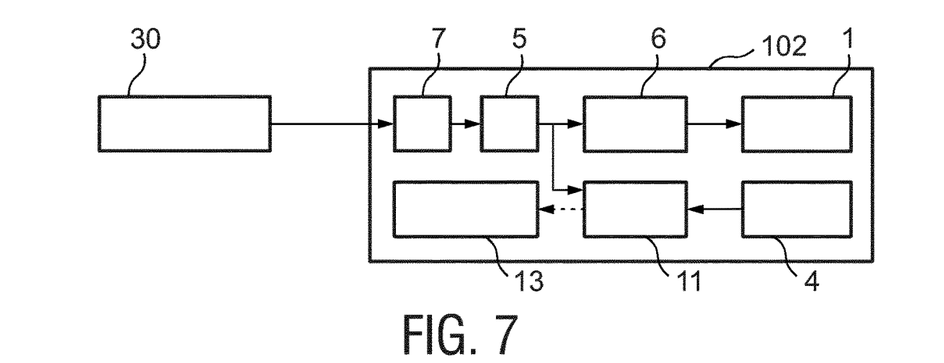
FIG. 7 shows a schematic diagram of a fifth embodiment of a sensor device and a communication device according to the present invention.

Another embodiment of a sensor device 102 is illustrated in FIG. 7. In this embodiment, the sensor device 102 is pre-configured with the interference spectra present in the environment in which it has been or will be used. Here, the interference spectra could be either obtained from a prior scan performed in the specific environment, or from information provided by the lighting vendors. A transmitting unit 30, which may also be part of a communication device as described above, transmits this information to the sensor device 102. Based on these interference spectra, the sensor device 102 can determine the optimal modulation mode or the optimum parameters of an interference reduction algorithm. If no appropriate modulation and/or reduction scheme can be found, the sensor device (e.g. pulse oximeter) or patient monitor may issue an interference alarm as described above.

Figure 8:
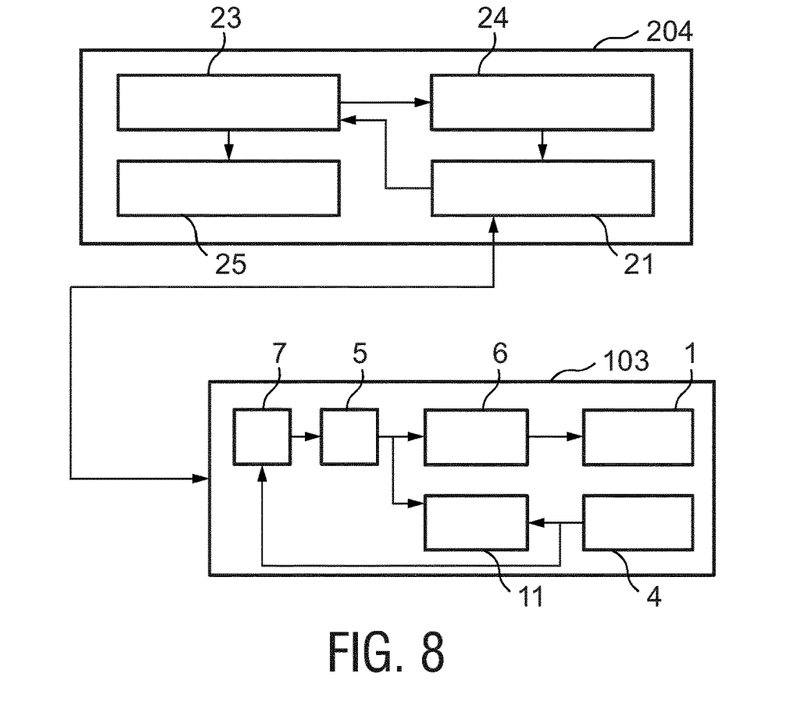
FIG. 8 shows a schematic diagram of a sixth embodiment of a sensor device and a communication device according to the present invention.

A still further embodiment of a communication device 204 and of a sensor device 103 is illustrated in FIG. 8. In this embodiment the ambient light measurement is performed by the photodiode 4 of the sensor device 103, which can for instance be done at start-up of the sensor device 103, or periodically while the sensor device 103 is operational. The sensor device (e.g. pulse oximetry module) sends the ambient light measurement to a patient monitor. The analysis of the ambient light spectrum and the subsequent selection and adjustment of the modulation mode and/or an interference reduction algorithm is done by the communication device 204, e.g. implemented as patient monitor. The analysis unit 23 of the communication device 204 analyses the ambient light spectrum and finds a suitable part in the spectrum containing the required bandwidth with a minimum amount of ambient light interference, possibly after interference reduction by an interference reduction algorithm with optimally selected parameters. The processing unit 24 determines the most appropriate modulation mode and/or interference reduction algorithm to use with the optimal parameters, also taking into account previously measured interference spectra. Subsequently, the communication device 21 transmits (e.g. broadcasts) a message to selected or, preferably, all sensor devices in the room, containing the instructions of the optimal modulation mode and/or interference reduction algorithm which should be selected and executed by the sensor device(s).

An interference reduction algorithm may in the simplest form be a low-pass filter which is applied to the demodulated PPG signals. If necessary, the cut-off frequency can be reduced to reduce interference near the pulse frequency components. The cut-off frequency can be part of or derived from the context information. Another example of an interference reduction algorithm is a notch filter which removes frequency components at one or more interfering frequencies specified by the context information. Still another example is an adaptive algorithm that estimates the interference present in the (de)modulated signal and subtracts the interference estimate to reduce the interference.

In another embodiment the context information may include sensor type information. Examples of sensor type information are information about whether the sensor is a transmissive or reflective sensor, about the sensor site (e.g. finger, forehead, earlobe, nasal septum, alar wing, foot), about the patient category (e.g. neonate, child, adult), about the manufacturer and model, etc. The sensor type information may thus be used to get information about the achievable performance, which could be stored in a table with achievable thresholds for specific sensor types. The sensor could thus e.g. set thresholds accordingly, i.e. use threshold that are adapted to the sensor type.

Figure 9:
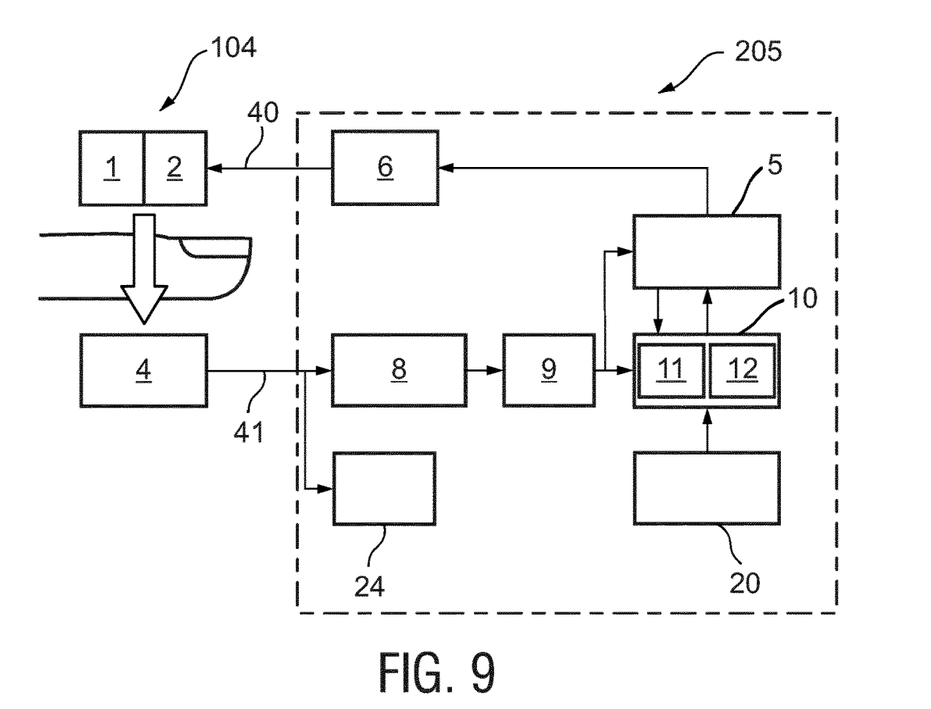
FIG. 9 shows a schematic diagram of a seventh embodiment of a sensor device and a communication device.

In the above explained embodiment the light modulator 6 and the light demodulator 11 are part of the sensor device. In other embodiments the light modulator 6 and the light demodulator 11 are part of the communication device. This is schematically illustrated in FIG. 9 showing a corresponding embodiment of a communication device 205 and another embodiment of a sensor device 104. As shown, the sensor device 104 merely comprises the light emitters 1, 2 and the light detector 4, whereas all other elements including the light modulator 6 and the light demodulator 11 are included in the communication device 205. Communication units (7, 21) as provided in the other embodiments are not necessarily required in this embodiment. The modulated drive currents of the light emitters 1, 2 are transmitted from the communication device 205 to the sensor device 104 via a connecting wire 40, and the detection signals of the light detector 4 are transmitted from the sensor device 104 to the communication device 205 via a connecting wire 41.

The communication device 205 (or any one of the above explained communication devices) may further comprise a processing unit for performing an interference reduction algorithm for reducing ambient light interference with settings indicated by or determined from the received context information and/or for processing the detected light in accordance with the sensor type information. Hence, the light modulation/demodulation and/or the processing may either be performed in the sensor device or in the communication device.

Because a communication device, such as a patient monitor, can remain in the same room, it can keep a history of ambient light spectra. In this way, the monitor can also store the interference from, e.g., a reading light which is only switched on occasionally. By taking into account the history in the determination of the most suitable modulation mode, the communication device can prevent disturbances from light sources which are switched on only occasionally.

Yet another embodiment of a communication device would be a smartphone or tablet, as coded light for example is specifically designed to be received by these devices. Sensor devices to perform for example spot-check measurements having communication means to connect to smartphones are widely available. By presetting the modulation based on context information gathered by the mobile device it connects to, the battery life or the number of spot-checks that can be performed on a single charge or battery could be improved in the end possibly resulting in again even smaller devices.

The present invention generally applies to all sensor devices, in particular pulse oximetry and photoplethysmography solutions, ranging from hospital sensors (such as hospital pulse oximeters), wearable sensors (such as wearable pulse oximeters, e.g. for telemetry or ambulatory monitoring), (sports) watches with optical heart rate technology, etc.

In summary, one embodiment of the present invention is directed to a sensor device for sensing physiological information of a subject comprising
- a communication unit for receiving, from an external source, context information indicating one or more of
  - a modulation mode,
  - settings of an interference reduction algorithm, and
  - spectral information indicating an ambient light spectrum, said spectral information allowing the sensor device to determine the modulation mode and/or settings of an interference reduction algorithm,
- one or more light emitters for emitting modulated light onto the tissue of the subject, and
- a light detector for detecting light which is transmitted through the tissue or/and which is reflected from the tissue, and
- a light modulator for modulating light in accordance with the modulation mode indicated by or determined from the received context information and a light demodulator for demodulating the detected light in accordance with the modulation mode used by the light modulator for modulating light.

Another embodiment of the present invention is directed to a sensor device for sensing physiological information of a subject comprising
- a communication unit for receiving, from an external source, context information indicating one or more of
  - a modulation mode,
  - settings of an interference reduction algorithm, and
  - spectral information indicating an ambient light spectrum, said spectral information allowing the sensor device to determine the modulation mode and/or settings of an interference reduction algorithm,
- one or more light emitters for emitting modulated light onto the tissue of the subject, and
- a light detector for detecting light which is transmitted through the tissue or/and which is reflected from the tissue, and
- a processing unit for performing an interference reduction algorithm for reducing ambient light interference with settings indicated by or determined from the received context information.

In still another embodiment the sensor device comprises such a light modulator and such a processing unit.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A sensor system for sensing physiological information of a subject, said system comprising:
   a first device, comprising:
   a context information obtaining unit for obtaining context information indicating spectral information indicating an ambient light spectrum, said spectral information allowing the sensor system to determine a modulation mode and/or settings of an interference reduction algorithm, wherein said context information obtaining unit comprises a first light detector, the first light detector configured for detecting the ambient light spectrum, wherein the ambient light spectrum is not transmitted through a tissue of the subject;
   a first communication unit for transmitting the obtained context information; and
   an analysis unit for analyzing the detected ambient light spectrum and generating said context information;
   wherein the first device is a lighting apparatus and said context information obtaining unit comprises an interface for receiving or measuring the emission spectrum of the lighting apparatus and generating said context information from said emission spectrum; and
   a second device, said second device being separate from the first device, and comprising:

a second communication unit for receiving, from the first communication unit, the transmitted context information;

one or more light emitters for emitting modulated light onto tissue of the subject;

a second light detector, the second light detector configured for detecting light which is transmitted through the tissue or/and which is reflected from the tissue; and further comprising: (i) a light modulator for modulating light in accordance with the modulation mode determined from the received context information and a light demodulator for demodulating the detected light in accordance with the modulation mode used by the light modulator for modulating light, and (ii) a processing unit for performing an interference reduction algorithm for reducing ambient light interference with settings indicated by or determined from the received context information;

wherein the first light detector of the first device is configured to detect the ambient light spectrum at least while no light is being emitted by said one or more light emitters of the second device;

wherein said processing unit of the second device is configured to determine, from the measured ambient light spectrum, the modulation mode and/or settings of the interference reduction algorithm such that said ambient light interference is minimized or is below a threshold determined based on said received context information and sensor type information for said second device; and wherein said processing unit of the second device is configured to determine if sufficient bandwidth is available for emitting light by the light emitter with ambient light interference below a predetermined threshold.

2. The sensor system as claimed in claim 1, wherein said processing unit of the second device is configured to determine a vital parameter of a subject from the received light.

3. The sensor system as claimed in claim 1, wherein the sensor system further comprises an alarm unit for issuing an alarm if it is determined that insufficient bandwidth is available for emitting light by the light emitter with ambient light interference below a predetermined threshold.

4. The sensor system as claimed in claim 1, wherein the first device comprises a processing unit for determining from the obtained context information the modulation mode and/or the settings of an interference reduction algorithm, for which ambient light interference is minimized or is below a predetermined threshold.

5. The sensor system as claimed in claim 1, wherein the first device comprises:

a processing unit for determining if sufficient bandwidth is available for emitting light by the light emitter of the second device with ambient light interference below a predetermined threshold, and an alarm unit for issuing an alarm if it is determined that insufficient bandwidth is available for emitting light by the light emitter of the second device with ambient light interference below a predetermined threshold.

6. The sensor system as claimed in claim 1, wherein the processing unit of the second device is configured to determine from received spectral information the modulation mode and/or settings of an interference reduction algorithm, for which ambient light interference is minimized or is below a predetermined threshold or a threshold determined from the context information.

7. The sensor system as claimed in claim 1, wherein said first light detector of the first device is configured to measure the ambient light spectrum while no light is emitted by said light emitter, and wherein said communication unit of the second device is configured to transmit further spectral information indicating the measured ambient light spectrum to an external entity.

8. The sensor system as claimed in claim 1, wherein the processing unit of the second device is configured for taking previously obtained spectral information and/or a previously determined modulation mode and/or previously determined settings of an interference reduction algorithm into account in determining the modulation mode and/or the settings of an interference reduction algorithm.

9. The sensor system of claim 1, wherein the first device is a patient monitor positioned in a room with the second device.

10. The sensor system of claim 1, wherein the first device is configured to store a history of ambient light spectra detected by the first light detector of the first device, and wherein the sensor system is configured to utilize at least some of the history of ambient light spectra for emitting modulated light by the second device.

11. The sensor system of claim 1, wherein the second device is a battery-powered device.

12. The sensor system of claim 1, wherein the first device is fixed in place relative to the subject.

13. The sensor system of claim 1, wherein the sensor system is preconfigured with information about ambient light interference present or potentially present within an environment that the sensor system is utilized.

14. A method for sensing physiological information of a subject, said method comprising:

receiving, by a light emitting device, context information indicating spectral information indicating an ambient light spectrum, said spectral information allowing the light emitting device to determine a modulation mode and/or settings of an interference reduction algorithm, wherein the context information is obtained by a first device comprising:

(i) a context information obtaining unit comprising a first light detector, the first light detector configured for detecting the ambient light spectrum, wherein the ambient light spectrum is not transmitted through a tissue of the subject; and (ii) a communication unit for transmitting the obtained context information to the light emitting device, wherein the light emitting device is separate from the first device;

emitting, by the light emitting device, modulated light onto the tissue of the subject; detecting, by a second light detector of the light emitting device, light which is transmitted through the tissue or/and which is reflected from the tissue;

modulating light in accordance with the modulation mode determined from the received spectral information and demodulating the detected light in accordance with the modulation mode, and/or performing the interference reduction algorithm for reducing ambient light interference with settings indicated by or determined from the received context information;

determining if sufficient bandwidth is available for emitting light by the light emitting device with ambient light interference below a predetermined threshold; and issuing an alarm if it is determined that insufficient bandwidth is available for emitting light by the light emitting device with ambient light interference below a predetermined threshold.

* * * * *